US00PP24650P3

(12) United States Plant Patent
Khemakongkanond

(10) Patent No.: US PP24,650 P3
(45) Date of Patent: Jul. 15, 2014

(54) ***DRACAENA* PLANT NAMED 'KKDR201206'**

(50) Latin Name: *Dracaena reflexa*
Varietal Denomination: KKDR201206

(71) Applicant: Kanachana Khemakongkanond, Bangkok (TH)

(72) Inventor: Kanachana Khemakongkanond, Bangkok (TH)

( * ) Notice: Subject to any disclaimer, the term of this patent is extended or adjusted under 35 U.S.C. 154(b) by 29 days.

(21) Appl. No.: 13/694,419

(22) Filed: Nov. 29, 2012

(65) Prior Publication Data

US 2014/0150150 P1 May 29, 2014

(51) Int. Cl.
*A01H 5/00* (2006.01)

(52) U.S. Cl.
USPC ..... Plt./383

(58) Field of Classification Search
CPC ..... A01H 5/02; A01H 5/00; A01H 5/12
USPC ..... Plt./383
See application file for complete search history.

*Primary Examiner* — Kent L Bell
(74) *Attorney, Agent, or Firm* — Cassandra Bright

(57) ABSTRACT

A new and distinct *Dracaena* cultivar named 'KKDR201206' is disclosed, characterized by distinctive foliage variegation pattern unlike other known *Draceana reflexa* cultivars, as well as strong stem and broad, outwardly oriented foliage. The new variety is a *Dracaena*, typically produced as an indoor ornamental plant.

1 Drawing Sheet

Latin name of the genus and species: *Dracaena reflexa*.
Variety denomination: 'KKDR201206'.

BACKGROUND OF THE INVENTION

The new cultivar is the product of chance discovery. The new variety originated as a naturally occurring, whole plant mutation of the unpatented 'Song of India' variety of *Dracaena reflexa*.

The new variety was first discovered by the inventor, Kanchana Khemakongkanond, a citizen of Thailand, in August of 2006, in a nursery in Bangkok, Thailand. After identifying the new variety as a potentially interesting selection, the inventor continued confidential testing and propagation of 'KKDR201206', assessing stability of the unique characteristics of this variety.

Asexual reproduction of the new cultivar 'KKDR201206' by vegetative cuttings was first performed at the same nursery in Bangkok, Thailand during January of 2006. Subsequently at least three generations have been produced from vegetative cuttings, and have shown that the unique features of this cultivar are stable and reproduced true to type.

SUMMARY OF THE INVENTION

The cultivar 'KKDR201206' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KKDR201206'. These characteristics in combination distinguish 'KKDR201206' as a new and distinct *Dracaena* cultivar:

1. Distinctive foliage variegation pattern unlike other known *Draceana reflexa* cultivars.
2. Strong stem.
3. Broad, outwardly facing foliage.

PARENT COMPARISON

Plants of the new cultivar 'KKDR201206' are similar to the unpatented 'Song of India' parent, in most horticultural characteristics. The new variety, however, produces foliage with a different variegation pattern than the parent. Additionally, foliage of the new variety has a different shape and orientation than the parent.

COMMERCIAL COMPARISON

The parent variety is the most similar commercial comparison.

BRIEF DESCRIPTION OF THE PHOTOGRAPH

The accompanying photograph in FIG. 1 illustrates in full color a typical plant of 'KKDR201206' grown in a commercial greenhouse in Honselersdijk, The Netherlands. This plant is approximately 6 months old, shown planted in a 12 cm. container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'KKDR201206' plants grown according to the following protocols.

Plants were grown in Honselersdijk, the Netherlands under greenhouse conditions, with temperatures ranging approximately from 25° C. to 36° C. during the day and 17° C. to 25°

C. at night with natural sunlight. Measurements and numerical values below represent averages of typical plant types.
Botanical classification: *Dracaena reflexa* 'KKDR201206'.

PROPAGATION

Propagation details:
Time to initiate rooting: About 6 weeks at approximately 25° C. to 28° C.
Root description: Moderately thick, moderately fibrous, not fleshy, young roots cream-white, older roots Greyed-Orange 163D.

PLANT

Age of plant described: 8 months.
Pot size of plant described: 17 cm circular pot.
Growth habit: Upright.
Height: Approximately 45.8 cm.
Plant spread: Approximately 39.0 cm.
Growth rate: Moderate, approximately 10 cm per month.
Branching characteristics: Not free branching, typically growing with one main stem from the base. Will only develop lateral branches after pinching/pruning.
Diameter of stem: Approximately 0.7 cm.
Internode length: Average 0.5 cm.
Texture of stem: Smooth, dull.
Color of stem: Green to yellow-green; near RHS 143A and 150B, both colors present, older stems Grey-brown; near RHS 199D.
Stem strength: Very strong.
Number of leaves per stem: Average 56.

FOLIAGE

Leaf:

*Arrangement*.—Alternate (spirally). Average Length: Approximately 13.9 cm. Average Width: Approximately 2.5 cm. Shape of blade: Lorate. Aspect: Leaves in an average angle of 65° to stem (=0). Apex: Acute. Base: Broad cuneate. Attachment: Sheathing. Margin: Entire. Texture of top surface: Smooth, moderately glossy. Texture of bottom surface: Smooth, moderately glossy.

*Color*.—Young foliage upper side: Green; near RHS 143A, tinged Green to Greyed-green; RHS 138B and 191A, both colors present, margin (average: 2.5 mm) Green; near RHS-143A, Yellow-green towards the base; near 144B and 144C, both colors present, whole leaf very narrowly margined (average 0.5 mm) green-white; 157B and 157D., both colors present. Young foliage under side: Green; near RHS 138B, margin (average: 2.5 mm) green; near RHS-143B, Yellow-green towards the base; near 145B, whole leaf very narrowly margined (average 0.5 mm) Green-white; 157B and 157D, both colors present. Mature foliage upper side: Greyed-green; near RHS N189A and N189B, both colors present, margin (average: 4 mm) Green; near RHS139A, the dark green margin and center are separated by a narrow (average 1 mm) line, colored Greyed-green; near RHS 192A and 192B, both colors present, whole leaf very narrowly margined (average 0.5 mm) Green-white; 157B and 157D, both colors present. Mature foliage under side: Greyed-green; near RHS 189A and 189B, both colors present, margin (average: 4 mm) Green; near RHS N137A and N137B, both colors present, the dark green margin and centre are separated by a narrow (average 1 mm) line, colored Greyed-green; near RHS 192B and 192D, both colors present, whole leaf very narrowly margined (average 0.5 mm) Green-white; 157B and 157D, both colors present.

*Venation*.—Type: Parallel. Color: Upperside: As leaf blade. Underside: As leaf blade.

*Sheath*.—Average Length: Approximately 0.4 cm. Average Width: Approximately 0.8 cm. Color: Yellow-green; near RHS 147D. Texture: Smooth, slightly glossy. Other Distinguishing Characteristics: No.

FLOWERING CHARACTERISTICS

Flowering not observed to date.

REPRODUCTIVE ORGANS

Not observed to date.

OTHER CHARACTERISTICS

Disease resistance: Good resistance to the normal diseases found in *Dracaena*.
Drought tolerance and cold tolerance: Normal for species, USDA zone 10 and higher.
Fruit/seed production: No fruits/seeds detected to date.

What is claimed is:

1. A new and distinct cultivar of *Dracaena* plant named 'KKDR201206' as herein illustrated and described.

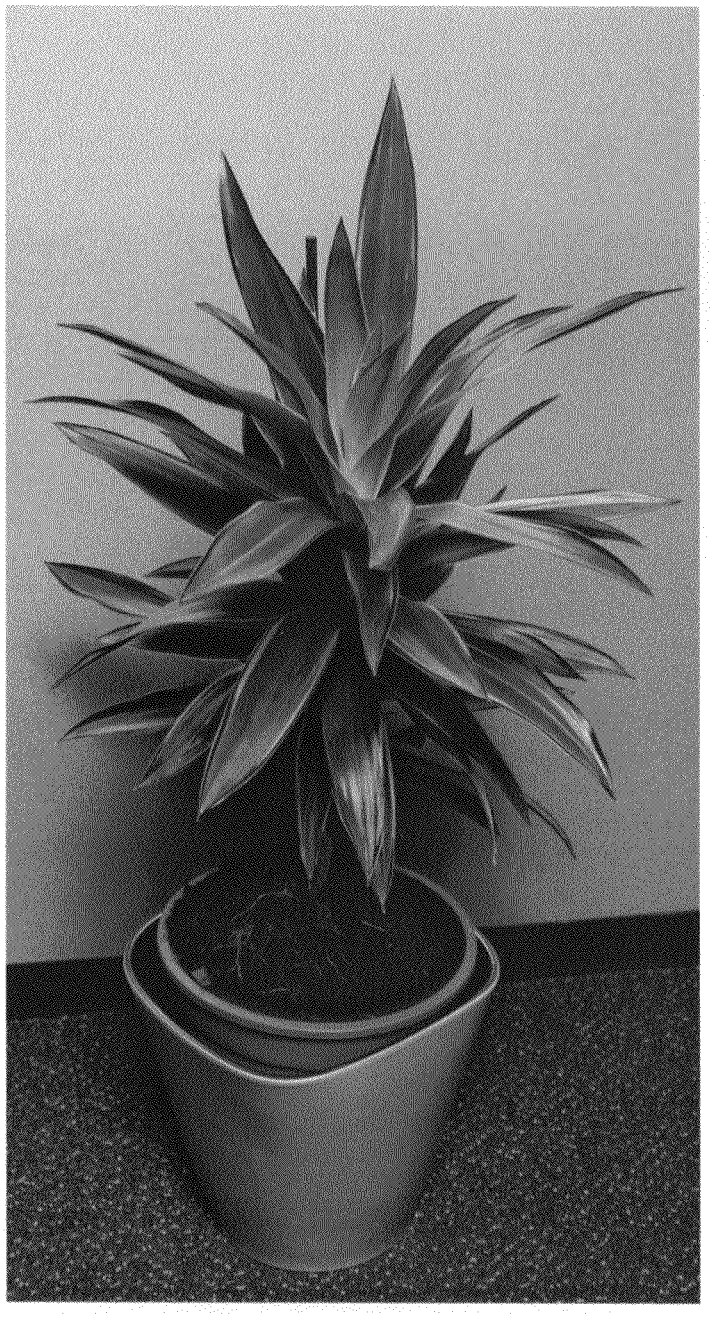

* * * * *